United States Patent [19]

Gay

[11] 3,950,444

[45] Apr. 13, 1976

[54] PROCESS FOR PREPARING ORTHO SUBSTITUTED ARYL FLUORIDES

[75] Inventor: Walter A. Gay, Cheshire, Conn.

[73] Assignee: Olin Corporation, New Haven, Conn.

[22] Filed: Aug. 30, 1974

[21] Appl. No.: 502,247

Related U.S. Application Data

[63] Continuation-in-part of Ser. No. 338,724, March 5, 1973, abandoned.

[52] U.S. Cl............ 260/650 F; 260/651 F; 260/900
[51] Int. Cl.$^2$......................................... C07C 25/13
[58] Field of Search.......... 260/650 F, 650 R, 651 F

[56] References Cited
UNITED STATES PATENTS

| | | | |
|---|---|---|---|
| 2,705,730 | 4/1955 | Head | 260/650 F |
| 3,160,623 | 12/1964 | Anello et al. | 260/650 F |

FOREIGN PATENTS OR APPLICATIONS

| | | | |
|---|---|---|---|
| 917,974 | 2/1963 | United Kingdom | 260/651 F |

*Primary Examiner*—D. Horwitz
*Attorney, Agent, or Firm*—Robert L. Andersen

[57] ABSTRACT

A process is provided for preparing ortho substituted aryl fluorides from corresponding diazonium fluorides. More particularly, the invention relates to a method for thermally decomposing diazonium fluorides substituted in the ortho position with halogen or trihalomethyl to a corresponding aryl fluoride. The method involves heating the diazonium fluoride to a temperature above its decomposition temperature and above the temperature at which the resulting product distills by contacting the same with a heat exchange medium at a temperature in the range of 100°–350°C.

8 Claims, No Drawings

PROCESS FOR PREPARING ORTHO SUBSTITUTED ARYL FLUORIDES

RELATED APPLICATION

The present invention is a continuation-in-part of U.S. Ser. No. 338,724, filed March 5, 1973 and now abandoned.

BACKGROUND OF THE INVENTION

1. Field of Invention

The present invention relates to preparation of ortho substituted aryl fluorides from corresponding diazonium fluorides. More particularly, the invention relates to a method for thermally decomposing such diazonium fluorides to form ortho substituted aryl fluorides wherein the ortho substituted entity is halogen or trihalomethyl.

2. Discussion of the Prior Art

Fluoroaromatic compounds prepared in accordance with the present invention are well known to be valuable intermediates in the manufacture of various dyes, agricultural pesticides, pharmeceutical and industrial compounds. For example, o-bromofluorobenzene may be converted to 3-fluorosalicylaldehyde for use in preparing oxygen absorbing solid state chelates such as "Fluomine" [cobalt-bis (3-fluorosalicylaldehyde) ethylenediimine].

The classical method for preparing aromatic fluorine compounds from aromatic amines is commonly referred to as the Schiemann method. This method is set forth in detail by Arthur Roe in *Organic Reactions* Vol. 5, Chapter 4, J. Wiley and Sons, Inc., New York (1949). In the Schiemann reaction the amine is diazotized to the corresponding diazonium fluoroborate. The diazonium fluoroborate is then isolated, purified and thermally decomposed. While quite satisfactory for the preparation of some compounds, the isolation, purification and particularly the thermal decomposition of many fluoroborates may be extremely hazardous due to a tendency to violently decompose. Methods have been devised to prevent violent decomposition but such methods involve a multiplicity of steps making the procedure an expensive one to practice.

A simpler, less dangerous method of converting aromatic amines to aryl fluorides is described in German Pat. No. 600,706. This method contemplates diazotization of the primary amine with sodium nitrite in anhydrous hydrogen fluoride. A solution is made of the primary amine and hydrogen fluoride and sodium nitrite is added to the mixture while temperature is maintained at about 5°C. Upon completion of diazotization the reaction mixture is refluxed at a temperature of about 30°–40°C. whereupon the diazonium fluoride decomposes to nitrogen and the corresponding aromatic fluoride. The principle disadvantage of this method is that it is not useful commercially preparing aryl fluorides which are substituted in the ortho position with groups which contain one or more atoms with unshared electron pairs. There are several reasons for this. First, the corresponding diazonium fluorides are generally stable at these temperatures leading to negligible or inadequate yields. The use of higher temperatures and pressures has been found to lead to the formation of a complex mixture of high melting solids, again producing inadequate yields. See Ferm, R. L. and Vander Werf, C. A., *J. Am. Chem. Soc.*, 72, 4809 (1950).

Anello et al., U.S. Pat. No. 3,160,623, teaches, with respect to derivatives other than the present ortho substituted derivatives, that decomposition of a diazonium fluoride prepared in the presence of a nitrosyl fluoride complex can advantageously be decomposed by heating the reaction mass to a temperature as high as 70°C. which is also high enough to effect evolution of nitrogen. According to this teaching yields are substantially decreased when temperatures above 70°C. are employed. Such temperatures, however, are inadequate to obtain satisfactory yields of the more stable ortho derivatives of the present invention.

It has now been discovered that by modifying thermal decomposition conditions these ortho substituted diazonium fluorides can be decomposed to provide high yields of corresponding ortho substituted aryl fluorides without forming excessive quantities of high melting solids.

SUMMARY OF THE INVENTION

In accordance with the present invention, there is provided a process for producing selected o-substituted aryl fluorides from corresponding diazonium fluorides which comprises contacting an ortho substituted aryl diazonium fluoride selected from the group consisting of o-haloaryl diazonium fluorides and o-trihalomethylaryl diazonium fluorides with a heat exchange medium in a decomposition zone at a temperature in the range of 100°–350°C., which temperature is above the temperature at which said diazonium fluoride decomposes and at least as high as the distillation temperature of the ortho substituted aryl fluoride formed upon decomposition, simultaneously removing said ortho substituted aryl fluoride as a distillate from said decomposition zone, and recovering said ortho substituted aryl fluoride from said distillate.

DESCRIPTION OF THE PREFERRED EMBODIMENTS

An ortho substituted aryl amine selected from the group consisting of o-haloanalines and o-trihalomethyl analines is converted to its corresponding diazonium fluoride by any known means. Preferably, the diazonium fluoride is formed in the reaction mixture by reacting the ortho substituted amine with sodium nitrite and excess hydrogen fluoride at a temperature of 0° ± 10°C.

In accordance with the present invention, a diazonium fluoride selected from the group consisting of o-halodiazonium fluorides and o-trihalomethyl diazonium fluorides is subjected to a temperature between 100° and 350°C. which is both above the decomposition temperature of the diazonium fluoride and at least as high as the distillation temperature of the ortho-substituted aryl fluoride formed upon decomposition of the diazonium fluoride. The decomposition is preferably conducted in a reaction or decomposition zone which may comprise any vessel adapted for the removal of product as it is formed. Since the temperature is above the distillation temperature of the resulting ortho substituted aryl fluoride, the vaporized reaction product is preferably removed from the decomposition zone as soon after its formation as possible, preferably simultaneously with its formation. It has been found that tar formation, which occurs at high temperatures as mentioned above, may be avoided or substantially decreased by promptly removing the decomposition product from the decomposition zone in order to minimize its availability for further reaction with the decomposing diazonium fluoride.

Minimum suitable temperatures for representative ortho-substituted aryl fluorides are shown below.

| DIAZONIUM FLUORIDE | PRODUCT | MIN TEMP(°C) |
|---|---|---|
| o-fluorobenzene | o-difluorobenzene | 100 |
| o-trifluoromethylbenzene | o-fluorobenzotrifluoride | 115 |
| o-chlorobenzene | o-chlorofluorobenzene | 138 |
| o-bromobenzene | o-bromofluorobenzene | 156 |
| o-iodobenzene | o-iodofluorobenzene | 188 |

It is to be understood that temperatures substantially in excess of those shown above may be employed if desired by the upper limit appears to be a matter of choice dictated generally by economic considerations rather than by any critical temperature limitation in the process. Therefore, I prefer to operate in a range of the minimum temperature shown above up to about 350°C. The temperatures shown are temperatures which are above the decomposition temperature of the diazonium fluoride and at least as high as the distillation temperature of the ortho substituted aryl fluoride being formed upon decomposition of the diazonium fluoride.

In the preferred embodiment of the invention, a reaction mixture containing the diazonium fluoride is transferred to a suitable reaction chamber where it is contacted with a heat exchange medium maintained at or above the temperature shown above. As the diazonium fluoride contacts the heat exchange medium, it is decomposed to the corresponding aryl fluoride with the evolution of nitrogen and the resulting aryl fluoride is preferably distilled off and recovered from the distillate by known means, for example, by neutralization then distillation.

Any known heat exchange medium that does not react with the diazonium fluoride at the selected temperature may be utilized. Examples of suitable heat exchange medium include: mineral oil, halocarbon oil, high boiling aliphatic or aromatic hydrocarbons either substituted or unsubstituted, sand, and heated metals.

In the preferred embodiment, the reaction mixture in which the diazonium fluoride is prepared is subjected to thermal decomposition without interposing the step of separating or purifying the diazonium fluoride. The invention, however, may be practiced by separating or purifying the diazonium compound or preforming it in any suitable manner and decomposing it in accordance with the method herein described.

The composition of the diazonium fluoride or starting amine will determine the ultimate product to be formed, a fluorine atom merely replacing the amino group of the corresponding aryl amine and the diazonium group of the intermediate diazonium fluoride as is well known to those skilled in this art. The diazonium fluorides or amines of the invention preferably have from 6–10 carbon atoms, for example, benzene, naphthalene. While 6–10 carbon atoms are preferred, it is contemplated that aromatic diazonium fluorides or amines having substantially more complex ring structures may be employed within the scope and spirit of the invention. For example, it is contemplated that steroids, benzothiadiazoles and other complex ring structures may be utilized to form derivatives thereof in accordance with the process of the invention.

Substituted on the ring carbon atom ortho to the amine or diazonium substituted carbon atom is a member of the group consisting of halogen and trihalomethyl and preferably selected from the group consisting of chlorine, bromine, fluorine, iodine, trichloromethyl, tribromomethyl, and trifluoromethyl. Thus, such starting materials as o-chloroaniline, o-bromoaniline, o-fluoroaniline, o-iodoaniline, o-aminobenzotrichloride, o-aminobenzotribromide and o-aminobenzotrifluoride are included. Each of these compounds contain substituents in the ortho position having unshared electron pairs making the usual methods for decomposition unsuitable as a means to commercially prepare the corresponding o-substituted aryl fluorides.

The aromatic ring of the starting material may also contain other substituents without interferring with the present reaction; for example, hydroxy, methoxy, or combinations thereof may be present in positions meta to the amino group, alkyls having from 1-12 carbon and preferably 1-4 carbon atoms halogens, trihalomethyl, nitro, carboxylic acid, lower alkyl esters of carboxylic acid or combinations of these may be present at any position other than the ortho position occupied by the substituent specified in the proceeding paragraph. It is to be noted that the specific substituents mentioned herein are representative of the types of substituents which can be utilized and are not intended as limitations of the scope of invention.

When treated in accordance with the present invention, such compounds as o-difluorobenzene, o-chlorofluorobenzene, o-bromofluorobenzene and o-fluorobenzotrifluoride and substituted derivatives thereof are obtained in high yields as shown in the accompanying examples.

EXAMPLE I

To 150 g (7.5 moles) anhydrous hydrogen fluoride, 64.5 g (0.38 mole) o-bromoaniline was added dropwise in 0.5–1.0 hour. While maintaining the reaction temperature at 0° ±5°C., 31.1 g (0.45 mole) sodium nitrite was added in portions over 0.5–1 hour with rapid stirring. The resulting o-bromobenzene diazonium fluoride containing reaction mixture was stirred for an additional 0.5 hour at 0°C. The reaction mixture was then refluxed for 1 hour. The mixture was then basified with 1.4 kg. 24% potassium hydroxide and steam distilled. Maximum yield of o-fluorobromobenzene was 3%.

EXAMPLE II o-bromobenzenediazonium fluoride was prepared as described in Example I. The reaction mixture was added over a 2-hour time period to 200–400 g of a heat exchange medium at 200°C. After basification of the distillate with 1.4 kg 24% potassium hydroxide o-bromofluorobenzene was recovered by steam distillation. The following results were obtained based on various heat exchange media used: sand, 53.1%; mineral oil, 60.8%; halocarbon oil, 63.1%; chlorinated paraffin oil, 66.4%.

EXAMPLE III o-chlorobenzenediazonium fluoride was prepared from 47.8 g (0.38 mole) chloroanaline, 31.1 g (0.45 mole) sodium nitrite and 150 g (7.5 mole) anhydrous hydrogen fluoride as described in Example I. After refluxing for 1 hour, basification with 1.4 kg 24% potassium hydroxide, and steam distillation a yield of 2% o-chlorofluorobenzene was obtained.

EXAMPLE IV

The intermediate o-chlorobenzenediazonium fluoride was prepared as described in Example III and added over a 2-hour time period to 200–400 g heat exchange medium at 200°C. After basification of the distillate with 1.4 kg 24% potassium hydroxide o-chlorofluorobenzene was obtained by steam distillation. Using sand as a heat exchange medium gave a yield of 10% o-chlorofluorobenzene whereas mineral oil gave a 27.9% yield.

EXAMPLE V o-trifluoromethylbenzene diazonium fluoride was prepared as described in Example I from 60.4 g (0.38 mole) o-aminobenzotrifluoride 31.1 g (0.45 mole) sodium nitrite and 150 g (7.5 mole) anhydrous hydrogen fluoride. After refluxing the reaction mixture for one hour, basifying it with a 1.4 kg 24% potassium hydroxide and steam distilling a maximum yield of 7% o-fluorobenzotrifluoride was obtained.

EXAMPLE VI

The intermediate, o-trifluoromethylbenzene fluoride was prepared as described in Example V and added over 2 hours to 200 g of mineral oil at 200°C. After basification with 1.4 kg. 24% potassium hydroxide and steam distillation, a yield of 53.1% o-fluorobenzotrifluoride was obtained.

I claim:

1. A process for preparing a selected ortho-substituted aryl fluoride having 6–10 ring carbon atoms and an ortho substitutent selected from the group consisting of halogen and trihalomethyl which comprises:

a. contacting a reaction mixture of a corresponding ortho-substituted aryl diazonium fluoride, with a heat exchange medium in a decomposition zone at a temperature in the range of 100-350°C., which temperatures is above the distillation temperature of the resulting ortho-substituted aryl fluoride, thereby decomposing said diazonium fluoride, b. simultaneously removing the resulting ortho-substituted aryl fluoride from said decomposition zone, and c. recovering said ortho-substituted aryl fluoride.

2. The process of claim 1 wherein said reaction mixture is added to said heat exchange medium and upon decomposition the resulting aryl fluoride simultaneously distilled off.

3. The process of claim 2 wherein said ortho-substituted aryl fluoride is an ortho-fluorobenzene substituted in the ortho position with a member of the group consisting of halogen and trihalomethyl.

4. The process of claim 3 wherein said aryl fluoride is o-difluorobenzene and said temperature is at least 100°C.

5. The process of claim 3 wherein said aryl fluoride is o-fluorobenzotrifluoride and said temperature is at least 115°C.

6. The process of claim 3 wherein said aryl fluoride is o-chlorofluorobenzene and said temperature is at least 138°C.

7. The process of claim 3 wherein said aryl fluoride is o-bromofluorobenzene and said temperature is at least 156°C.

8. The process of claim 3 wherein said aryl fluoride is o-iodofluorobenzene and said temperature is at least 188°C.

* * * * *

PO-1050
(5/69)

UNITED STATES PATENT OFFICE
CERTIFICATE OF CORRECTION

Patent No. 3,950,444    Dated April 13, 1976

Inventor(s) WALTER A. GAY

It is certified that error appears in the above-identified patent and that said Letters Patent are hereby corrected as shown below:

In column 3, line 17, the word "by" should read --but--.

In column 5, line 25, after the word "o-trifluoromethylbenzene" insert --diazonium--.

Signed and Sealed this twenty-ninth Day of June 1976

[SEAL]

Attest:

RUTH C. MASON
Attesting Officer

C. MARSHALL DANN
Commissioner of Patents and Trademarks